(12) United States Patent
Pitzele et al.

(10) Patent No.: US 6,956,131 B2
(45) Date of Patent: Oct. 18, 2005

(54) 2-AMINO-3, 4 HEPTENOIC COMPOUNDS USEFUL AS NITRIC OXIDE SYNTHASE INHIBITORS

(75) Inventors: Barnett S. Pitzele, Skokie, IL (US); James A. Sikorski, Kirkwood, MO (US); Ronald Keith Webber, St. Charles, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/834,815

(22) Filed: Apr. 13, 2001

(65) Prior Publication Data

US 2002/0072542 A1 Jun. 13, 2002

Related U.S. Application Data

(60) Provisional application No. 60/196,940, filed on Apr. 13, 2000.

(51) Int. Cl.[7] ............................................. C07C 251/00
(52) U.S. Cl. ....................................................... 562/560
(58) Field of Search ................................ 562/560, 561, 562/564

(56) References Cited

U.S. PATENT DOCUMENTS

| | | | |
|---|---|---|---|
| 5,132,453 A | 7/1992 | Griffith ........................ | 562/560 |
| 5,684,008 A | 11/1997 | Hallinan et al. ............ | 514/256 |
| 5,830,917 A | 11/1998 | Moore et al. ............... | 514/634 |
| 5,854,251 A | 12/1998 | Hallinan et al. ............ | 514/256 |
| 5,863,931 A | 1/1999 | Beams et al. ............... | 514/357 |
| 5,919,787 A | 7/1999 | Hallinan et al. ............ | 514/256 |
| 5,945,408 A | 8/1999 | Webber et al. .............. | 514/63 |
| 5,981,511 A | 11/1999 | Gapud et al. ............... | 514/63 |
| 5,994,391 A | 11/1999 | Lee et al. .................... | 514/431 |
| 6,169,089 B1 | 1/2001 | Hallinan et al. ............ | 514/256 |
| 6,344,483 B1 * | 2/2002 | Hallinan et al. | |

FOREIGN PATENT DOCUMENTS

| | | | |
|---|---|---|---|
| EP | 04 46699 | 5/2000 | ............ C07K/5/06 |
| EP | 05 21471 | 10/2000 | .......... C07D/239/42 |
| WO | WO 93 13055 | 7/1993 | .......... C07C/257/14 |
| WO | WO 93 16055 | 8/1993 | .......... C07D/281/10 |
| WO | WO 94 12165 | 6/1994 | .......... A61K/31/155 |
| WO | WO 94 14780 | 7/1994 | .......... C07D/239/48 |
| WO | WO 95 11014 | 4/1995 | .......... A61K/31/00 |
| WO | WO 95 11231 | 4/1995 | .......... C07D/207/22 |
| WO | WO 95 25382 | 9/1995 | .......... H03H/17/02 |
| WO | WO 95 25717 | 9/1995 | .......... C07C/257/14 |
| WO | WO 95/25717 A1 * | 10/1995 | |
| WO | WO 96 15120 | 5/1996 | .......... C07D/257/06 |
| WO | WO 96 33175 | 10/1996 | .......... C07D/223/12 |
| WO | WO 96 35677 | 11/1996 | .......... C07D/223/12 |
| WO | WO 97 06802 | 2/1997 | .......... A61K/31/495 |
| WO | WO 99 29865 | 6/1999 | .......... C12N/15/28 |
| WO | WO 99 46240 | 9/1999 | .......... C07C/257/14 |

OTHER PUBLICATIONS

S. Moncada and E. Higgs, *Molecular Mechanisms and Therapeutic Strategies Related to Nitric Oxide* 1995, FASEB J., 9, 1319–1330.

S. Rozen, I. Shahak, and E. Bergmann, *Organic Fluorine Compounds Part XLIV, Preparation and Reactions of Epifluorohydrin* 1971, Synthesis 646–7.

E. Bergmann, S. Cohen, and I. Shahak, *Organic Fluorine Compounds. Part XX. Some Reactions of 1–Chloro–3–fluoropropan–2–ol and Epifluorohydrin* 1961, J Chem Soc 3448–52.

A. Jeanguenat and D. Seebach, *Stereoselective Chain Elongation at C–3 of Cysteine through 2,3–Dihydrothiazoles, Without Racemization. Preparation of 2–Amino–5–hydroxy–3–mercapto alkanoic Acid Derivatives.* 1991, J. Chem. Soc. Perkin Trans. 1, 2291–8.

G. Pattenden, S. Thom, and M. Jones, *Enantioselective Synthesis of 2–Alkyl Substituted Cysteines.* 1993, Tetrahedron, 49, 2131.

D. Bredt and S. Snyder, *Isolation of nitric oxide synthetase, a calmodulin–requiring enzyme.* 1990 Proc. Natl. Acad. Sci. U.S.A., 87, 682–685.

Moore et al, *2–Iminopiperidine and Other 2–Iminoazaheterocycles as Potent Inhibitors of Human Nitric Oxide Synthase Isoforms* 1996 J. Med. Chem., 39, 669–672.

T. Misko et al, *A Fluorometric Assay for the Measurement of Nitrite in Biological Samples* 1993, Analytical Biochemistry, 214, 11–16.

Y. Lee et al., *Conformationally–restricted Arginine Analogues as Alternative Substrates and Inhibitors of Nitric Oxide Synthases* 1999 Bioorg. Med. Chem. 7 1097–1104.

R. Young et al., *Inhibition of Inducible Nitric Oxide Synthase by Acetamidine Derivatives of Hetero–Substituted Lysine and Homolysine* 2000 Bioorg. Med. Chem. Lett. 10 597–600.

* cited by examiner

Primary Examiner—Paul A. Zucker
(74) *Attorney, Agent, or Firm*—Philip B. Polster, II

(57) ABSTRACT

The present invention is directed to a compound of formula I:

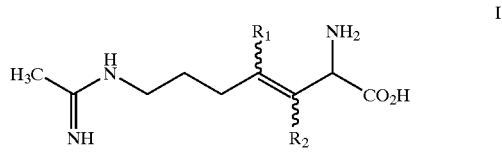

or a pharmaceutically acceptable salt thereof, wherein:

$R_2$ is selected from the group consisting of H and methyl; and
$R_2$ is selected from the group consisting of H and methyl.

The compounds possess useful nitric oxide synthetase inhibiting activity, and are expected to be useful in the treatment or prophylaxis of a disease or condition in which the synthesis or over synthesis of nitric oxide forms a contributory part.

12 Claims, No Drawings

2-AMINO-3, 4 HEPTENOIC COMPOUNDS USEFUL AS NITRIC OXIDE SYNTHASE INHIBITORS

This application claims the priority of U.S. Provisional Application Ser. No. 60/196,940 filed Apr. 13, 2000.

BACKGROUND OF THE INVENTION

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

The following individual publications disclose compounds that inhibit nitric oxide synthesis and preferentially inhibit the inducible isoform of nitric oxide synthase:

PCT Patent Application Ser. No. WO 96/35677.
PCT Patent Application Ser. No. WO 96/33175.
PCT Patent Application Ser. No. WO 96/15120.
PCT Patent Application Ser. No. WO 95/11014.
PCT Patent Application Ser. No. WO 95/11231.
PCT Patent Application Ser. No. WO 99/46240.
PCT Patent Application Ser. No. WO 95/24382.
PCT Patent Application Ser. No. WO 94/12165.
PCT Patent Application Ser. No. WO 94/14780.
PCT Patent Application Ser. No. WO 93/13055.
PCT Patent Application Ser. No. WO 99/62875.
European Patent Ser. No. EP0446699A1.
U.S. Pat. No. 5,132,453.
U.S. Pat. No. 5,684,008.
U.S. Pat. No. 5,830,917.
U.S. Pat. No. 5,854,251.
U.S. Pat. No. 5,863,931.
U.S. Pat. No. 5,919,787.
U.S. Pat. No. 5,945,408.
U.S. Pat. No. 5,981,511.

PCT Patent Application Ser. No. WO 95/25717 discloses certain amidino derivatives as being useful in inhibiting inducible nitric oxide synthase.

PCT Patent Application Ser. No. WO 99/62875 discloses further amidino compounds as being useful in inhibiting inducible nitric oxide synthase.

In particular, WO 93/13055 discloses compounds of the formula

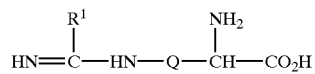

and salts, and pharmaceutically acceptable esters and amides thereof, in which:

$R^1$ is a $C_{1-6}$ straight or branched chain alkyl group, a $C_{2-6}$ alkenyl group, a $C_3$–$C_6$cycloalkyl group or a $C_{3-6}$ cycloalkyl $C_{1-6}$alkyl group;

Q is an alkylene, alkenylene or alkynylene group having 3 to 6 carbon atoms and which may optionally be substituted by one or more $C_{1-3}$ alkyl groups; a group of formula —$(CH_2)_pX(CH_2)_q$— where p is 2 or 3, q is 1 or 2 and X is $S(O)_x$ where x is 0, 1 or 2, O or $NR^2$ where $R^2$ is H or $C_{1-6}$alkyl; or a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$alkyl, $C_{1-6}$alkoxy, hydroxy, halo, nitro, cyano, trifluoro $C_{1-6}$alkyl, $C_{1-6}$ alkoxy, hydroxy, halo, nitro, cyano, trifluoro$C_{1-6}$alkyl, amino, $C_{1-6}$alkylamino or di$C_{1-6}$alkylamino.

Various attempts have been made to improve the potency and selectivity of NOS inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000))

teach that imposing conformational rigidity with one or more carbon—carbon double bonds is not a favorable approach to impart selectivity for NOS inhibitors.

SUMMARY OF THE INVENTION

Compounds have now been found which have the advantage of being very efficacious in the human cartilage explant assay, a model for osteoarthritis.

The present invention demonstrates that a carbon—carbon double bond can be used as a rigidifying element, and the resulting compounds have unexpected potency and selectivity for inhibition of inducible NOS.

Moreover, the publication by Y. Lee et al (*Bioorg. Med. Chem.* 7, 1097 (1999)) teaches that when a carbon—carbon double bond is used to constrain the arginine backbone, the geometric isomer placing the carbon framework in a cis or Z orientation produces a less favorable interaction with NOS. In contrast, olefinic derivatives of arginine placing the carbon framework in the trans or E configuration are better substrates. The present invention demonstrates that a carbon—carbon double bond imparts a highly favorable interaction with inducible NOS, such that the resulting compounds have unexpected potency and selectivity for inhibition of inducible NOS over the constitutive isoforms.

In a broad embodiment, the present invention is directed to novel compounds, pharmaceutical compositions and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthetase inhibiting activity, and are expected to be useful in the treatment or prophylaxis of a disease or condition in which the synthesis or over synthesis of nitric oxide forms a contributory part.

In one embodiment of the present invention, the compounds are represented by Formula I, II or III

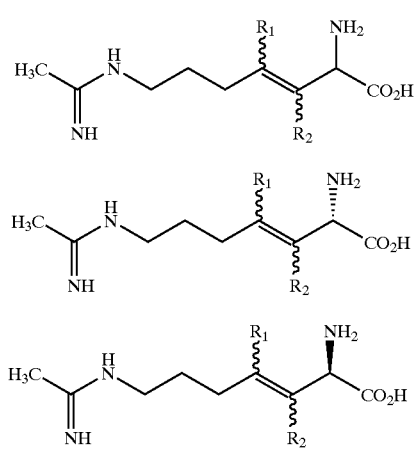

or a pharmaceutically acceptable salt thereof, wherein:

$R_1$ is hydrogen or methyl;
$R_2$ is hydrogen or methyl.

In another embodiment of Formula I, II or III, the compounds are represented wherein:

$R_1$ is hydrogen; and
$R_2$ is hydrogen or methyl.

In another embodiment of Formula I, II or III, the compounds are represented wherein:

$R_1$ is hydrogen; and
$R_2$ is methyl.

In another embodiment the compounds are represented by Formula I, II or III wherein:

$R_1$ is hydrogen; and
$R_2$ is hydrogen.

Formula I, II or III may also be represented wherein:

$R_1$ is methyl; and
$R_2$ is hydrogen or methyl.

Another embodiment of the invention is Formula I, II or III wherein:

$R_1$ is methyl; and
$R_2$ is hydrogen.

The compounds of Formula I, II or III may also be represented wherein:

$R_1$ is methyl; and
$R_2$ is methyl.

The compounds may also be represented wherein:

$R_1$ is hydrogen or methyl; and
$R_2$ is hydrogen.

In addition, the present invention includes the E and Z isomers of Formula I, II, and III.

Methods of using the compounds of Formula I, II and III include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, II or III, lowering nitric oxide levels in a subject in need of such by administering a therapeutically effective amount of a compound of Formula I, II or III, lowering nitric oxide levels in a subject in need of such by administering a therapeutically effective amount of a pharmaceutical composition comprising a compound of Formula I, II or III.

DETAILED DESCRIPTION OF THE INVENTION

In one embodiment of the present invention, the compounds are represented by Formula I, II or III

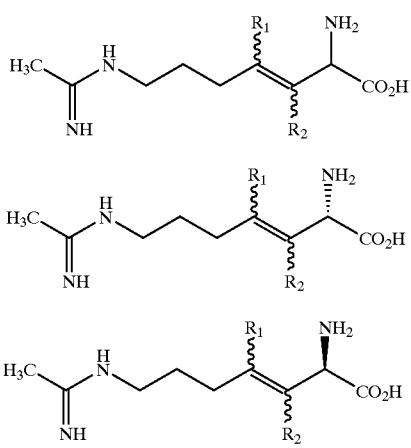

or a pharmaceutically acceptable salt thereof, wherein:

$R_1$ is hydrogen or methyl;
$R_2$ is hydrogen or methyl.

In another embodiment of Formula I, II or III, the compounds are represented wherein:

$R_1$ is hydrogen; and
$R_2$ is hydrogen or methyl.

In another embodiment of Formula I, II or III, the compounds are represented wherein:

$R_1$ is hydrogen; and
$R_2$ is methyl.

In another embodiment the compounds are represented by Formula I, II or III wherein:

$R_1$ is hydrogen; and
$R_2$ is hydrogen.

Formula I, II or III may also be represented wherein:

$R_1$ is methyl; and
$R_2$ is hydrogen or methyl.

Another embodiment of the invention is Formula I, II or III wherein:

$R_1$ is methyl; and
$R_2$ is hydrogen.

The compounds of Formula I, II or III may also be represented wherein:

$R_1$ is methyl; and
$R_2$ is methyl.

The compounds may also be represented wherein:

$R_1$ is hydrogen or methyl; and
$R_2$ is hydrogen.

In addition, the present invention includes the E and Z isomers of Formula I, II, and III.

Methods of using the compounds of Formula I, II and III include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, II or III, lowering nitric oxide levels in a subject in need of such by administering a therapeutically effective amount of a compound of Formula I, II or III, lowering nitric oxide levels in a subject in need of such by administering a therapeutically effective amount of a pharmaceutical composition comprising a compound of Formula I, II or III.

Also included in the family of compounds of Formula I, II or III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I, II or III may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula I, II or III include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula I, II or III by reacting, for example, the appropriate acid or base with the compound of Formula I, II or III.

While it may be possible for the compounds of Formula I, II or III to be administered as the raw chemical, it is preferable to present them as a pharmaceutical composition. According to a further aspect, the present invention provides a pharmaceutical composition comprising a compound of Formula I, II or III or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of Formula I, II or III or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 0.5 mg to 200 mg, usually around 0.5 mg to 100 mg.

The compounds of Formula I, II or III are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers and mixtures thereof, E- and Z-geometric isomers and mixtures thereof, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis" or "Z") or on opposite sides of the double bond ("trans" or "E"). Some of the compounds described contain alkenyl groups, and are meant to include both cis and trans or "E" and "Z" geometric forms. Other compounds of the invention include mixtures of both the cis/Z and the trans/E isomers.

Some of the compounds described contain one or more stereocenters and are meant to include R, S, and mixtures of R and S forms for each stereocenter present. Some of the compounds described contain one or more geometric isomers and are meant to include E, Z and mixtures of E and Z forms for each stereocenter present.

The following general synthetic schemes are useful in making the present invention.

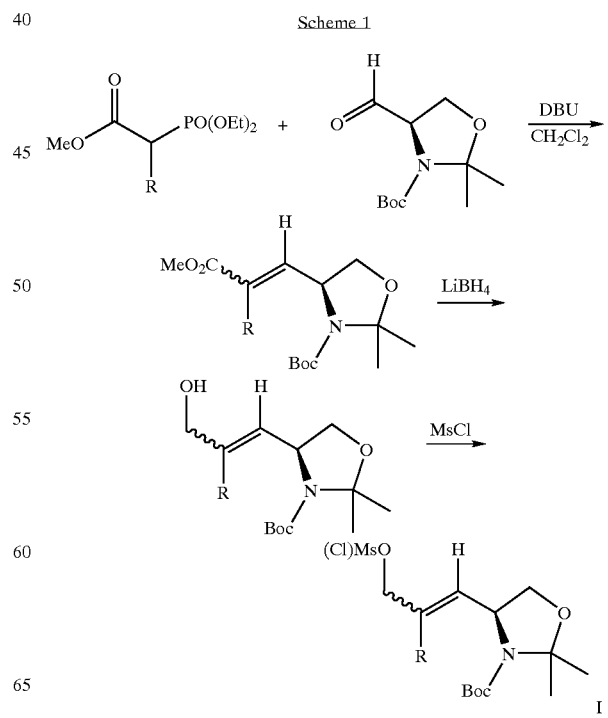

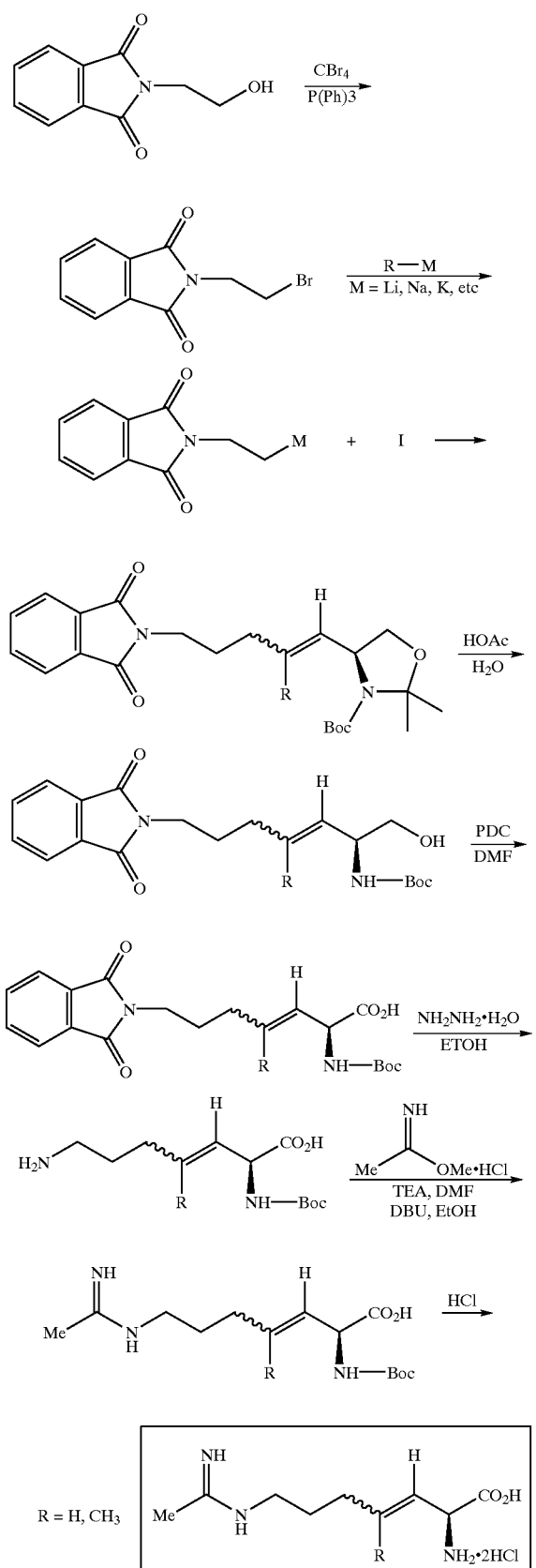
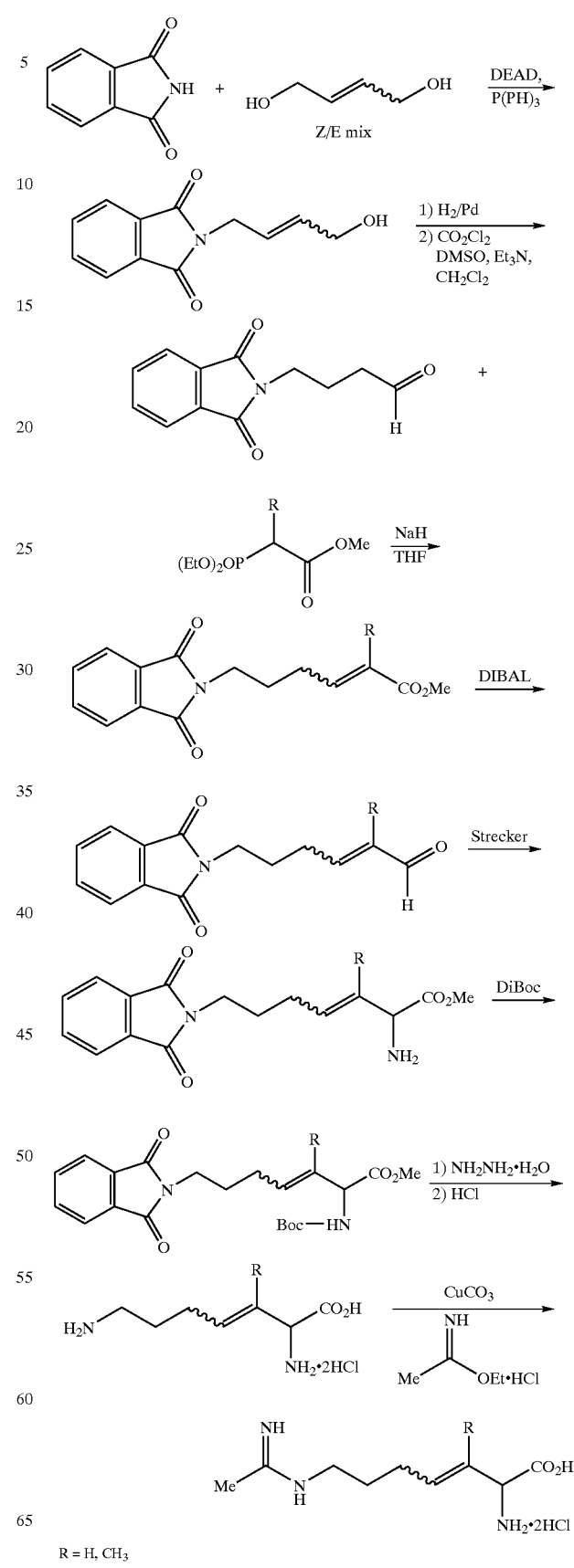
Scheme 2
R = H, CH₃

Scheme 3

R[1] = H, CH$_3$
R[2] = H, CH$_3$
X = leaving group

The following examples can be made using the preceding synthetic schemes and are provided to illustrate the present invention and not intended to limit the scope thereof. Those skilled in the art will readily understand that known variations of the conditions and processes of the preparative procedures can be used to prepare these compounds.

EXAMPLE 1

(2S,3E)-2-amino-7-[(1-iminoethyl)amino]-3heptenoic acid, dihydrochloride

EXAMPLE 2

(2S,3Z)-2-amino-7-[(1-iminoethyl)amino]-3heptenoic acid, dihydrochloride

EXAMPLE 3

(3E)-2-amino-3-methyl-7-[(1-iminoethyl)amino]-3heptenoic acid, dihydrochloride

EXAMPLE 4

(3Z)-2-amino-3methyl-7-[(1-iminoethyl)amino]-3heptenoic acid, dihydrochloride

EXAMPLE 5

(3E)-2-amino-3,4-dimethyl-7-[(1-iminoethyl)amino]-3heptenoic acid, dihydrochloride

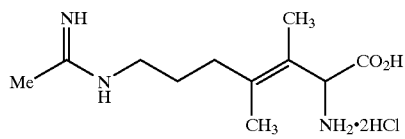

EXAMPLE 6

(3Z)-2-amino-3,4-dimethyl-7-[(1-iminoethyl)amino]-3heptenoic acid, dihydrochloride

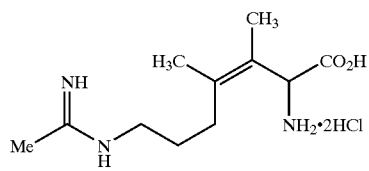

EXAMPLE 7

(3E)-2-amino-4-methyl-7-[(1-iminoethyl)amino]-3heptenoic acid, dihydrochloride

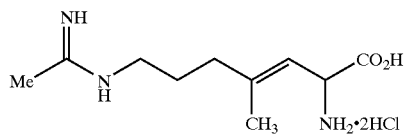

EXAMPLE 8

(3Z)-2-amino-4-methyl-7-[(1-iminoethyl)amino]-3heptenoic acid, dihydrochloride

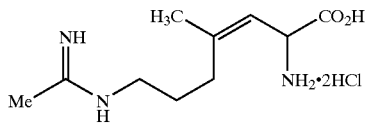

EXAMPLE 9

(2R,3E)-2-amino-7-[(1-iminoethyl)amino]-3heptenoic acid, dihydrochloride

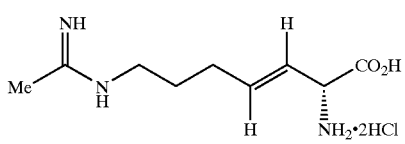

EXAMPLE 10

(2R,3Z)-2-amino-7-[(1-iminoethyl)amino]-3heptenoic acid, dihydrochloride

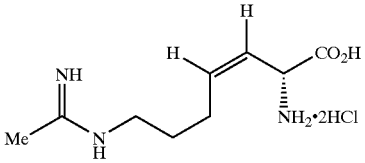

The activity of the above listed compounds can be determined in the following assays:

Citrulline Assay for Nitric Oxide Synthase

Nitric oxide synthase (NOS) activity is measured by monitoring the conversion of [$^3$H]-arginine to [$^3$H]-citrulline (Bredt and Snyder, *Proc. Natl. Acad. Sci. U.S.A.*, 87, 682–685, 1990 and Misko et al, *Eur. J. Pharm.*, 233, 119–125, 1993). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a lambda cDNA library made from RNA extracted from a colon sample from a patient with ulcerative colitis. The cDNA for human endothelial constitutive NOS (hecNOS) is isolated from a lambda cDNA library made from RNA extracted from human umbilical vein endothelial cells (HUVEC) and the cDNA for human neuronal constitutive NOS (hncNOS) is isolated from a lambda cDNA library made from RNA extracted from human cerebellum obtained from a cadaver. The recombinant enzymes are expressed in Sf9 insect cells using a baculovirus vector (Rodi et al, in *The Biology of Nitric Oxide. Pt. 4: Enzymology Biochemistry and Immunology*; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 $\mu$L of enzyme is added to 40 $\mu$L of 50 mM Tris (pH 7.6) in the presence or absence of test compounds and the reaction initiated by the addition of 50 $\mu$L of a reaction mixture containing 50 mM Tris (pH 7.6), 2.0 mg/mL bovine serum albumin, 2.0 mM DTT, 4.0 mM CaCl$_2$, 20 $\mu$M FAD, 100 $\mu$M tetrahydrobiopterin, 0.4–2.0 mM NADPH and 60 $\mu$M L-arginine containing 0.9 $\mu$Ci of L-[2,3-$^3$H]-arginine. The final concentration of L-arginine in the assay is 30 $\mu$M. For hecNOS or hncNOS, calmodulin is included at a final concentration of 40–100 nM. Following incubation at 37° C. for 15 minutes, the reaction is terminated by addition of 300 $\mu$L of cold stop buffer containing 10 mM EGTA, 100 mM HEPES, pH 5.5 and 1 mM citrulline. [3H]-Citrulline is separated by chromatography on Dowex 50W X-8 cation exchange resin and radioactivity determined with a liquid scintillation counter. Results are reported as the IC$_{50}$ values of compounds for hiNOS, hecNOS and hncNOS.

In Vivo Assay

Rats are treated with an intraperitoneal injection of 10–12.5 mg/kg of endotoxin (LPS) to induce systemic expression of inducible nitric oxide synthase, resulting in markedly elevated plasma nitrite/nitrate levels. Compounds are administered orally 1 hour prior to LPS administration and plasma nitrite/nitrate levels are determined 5 hours following LPS administration.

Raw Cell Nitrite Assay

RAW 264.7 cells can be plated to confluency on a 96-well tissue culture plate grown overnight (17 h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 mL of buffer containing L-arginine (30 mM) +/– inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite. T. P. Misko et al, *Analytical Biochemistry*, 214, 11–16 (1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 25–45 mg in weight and one or two explants per well are placed into 48 well culture plates with 500 μL of culture media per well. The culture media was a custom modification of Minimum Essential Medium(Eagle) with Earle's salts (GibcoBRL) prepared without L-Arginine, without L-Glutamine and without phenol red and supplemented before use with 100 μM L-Arginine (Sigma), 2 mM L-glutamine, 1X HL-1 supplement (BioWhittaker), 50 mg/ml ascorbic acid (Sigma) and 150 pg/ml recombinant human IL-1β (RD Systems) to induce nitric oxide synthase. Compounds are then added in 10 μL aliquots and the explants incubated at 37 degrees C. with 5% $CO_2$ for 18–24 hours. The day old supernatant is then discarded and replaced with fresh culture media containing recombinant human IL-1β and compound and incubated for another 20–24 hours. This supernatant is analyzed for nitrite with a fluorometric assay (Misko et al, *Anal. Biochem.*, 214, 11–16, 1993). All samples are done in quadruplicate. The explants are weighed and the nitrite levels normalized to weight. Unstimulated controls are cultured in media in the absence of recombinant human IL-1 β. $IC_{50}$ values are determined from plotting the percent inhibition of nitrite production at six different concentrations of inhibitor.

What is claimed is:

1. A compound of formula I

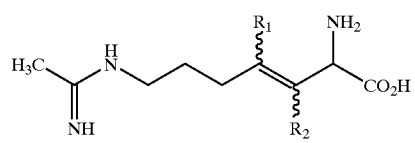

or a pharmaceutically acceptable salt thereof, wherein:
$R_1$ is H; and
$R_2$ is methyl.

2. A compound of formula I

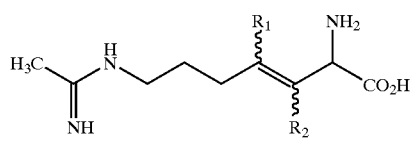

or a pharmaceutically acceptable salt thereof, wherein:
$R_1$ is methyl; and
$R_2$ is selected from the group consisting of hydrogen and methyl.

3. A compound of formula I

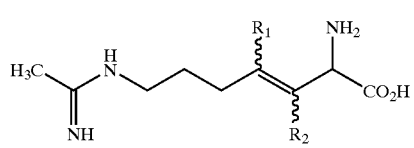

or a pharmaceutically acceptable salt thereof, wherein:
$R_1$ is methyl; and
$R_2$ is hydrogen.

4. A compound of formula I

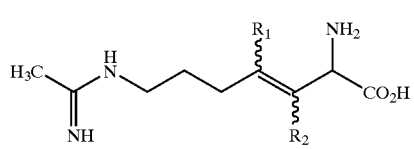

or a pharmaceutically acceptable salt thereof, wherein:
$R_1$ is methyl; and
$R_2$ is methyl.

5. A compound of Formula II

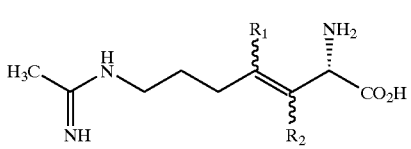

or a pharmaceutically acceptable salt thereof, wherein:
$R_1$ is H; and
$R_2$ is methyl.

6. A compound of Formula II

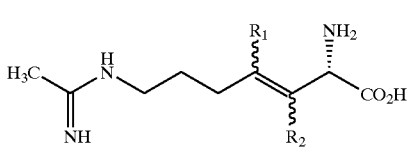

or a pharmaceutically acceptable salt thereof, wherein:
$R_1$ is methyl; and
$R_2$ is selected from the group consisting of H and methyl.

7. A compound of Formula II

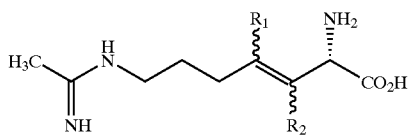

or a pharmaceutically acceptable salt thereof, wherein:
$R_1$ is methyl; and
$R_2$ is H.

8. A compound of Formula II

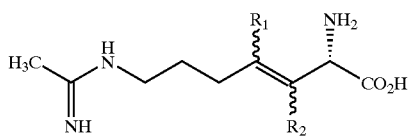

or a pharmaceutically acceptable salt thereof, wherein:
$R_1$ is methyl; and
$R_2$ is methyl.

9. A compound of formula III

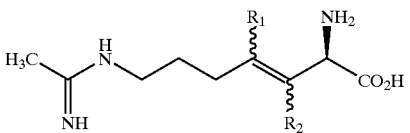

or a pharmaceutically acceptable salt thereof, wherein:
$R_1$ is H; and
$R_2$ is methyl.

10. A compound of formula III

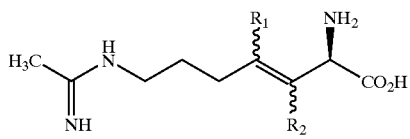

or a pharmaceutically acceptable salt thereof, wherein:
$R_1$ is methyl; and
$R_2$ is selected from the group consisting of hydrogen and methyl.

11. A compound of formula III

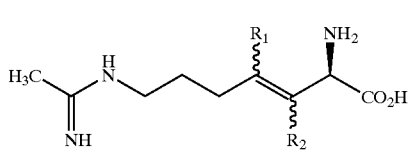

or a pharmaceutically acceptable salt thereof, wherein:
$R_1$ is methyl; and
$R_2$ is H.

12. A compound of formula III

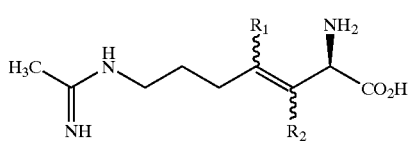

or a pharmaceutically acceptable salt thereof, wherein:
$R_1$ is methyl; and
$R_2$ is methyl.

* * * * *